US010906950B2

(12) United States Patent
Bonnaillie et al.

(10) Patent No.: US 10,906,950 B2
(45) Date of Patent: Feb. 2, 2021

(54) ALKALINE PH-MODIFIED EDIBLE CASEIN-BASED FILMS AND COATINGS, AND METHOD FOR THE MAKING THEREOF

(71) Applicant: The United States of America, as represented by the Secretary of Agriculture, Washington, DC (US)

(72) Inventors: Laetitia Bonnaillie, West Chester, PA (US); Peggy M. Tomasula, Titusville, NJ (US)

(73) Assignee: The United States of America as Represented by the Secretary of Agriculture, Washington, DC (US)

( * ) Notice: Subject to any disclaimer, the term of this patent is extended or adjusted under 35 U.S.C. 154(b) by 244 days.

(21) Appl. No.: 15/679,431

(22) Filed: Aug. 17, 2017

(65) Prior Publication Data

US 2018/0051062 A1    Feb. 22, 2018

Related U.S. Application Data

(60) Provisional application No. 62/377,288, filed on Aug. 19, 2016.

(51) Int. Cl.
| | | |
|---|---|---|
| *C07K 14/47* | (2006.01) | |
| *C08J 5/18* | (2006.01) | |
| *C08K 5/053* | (2006.01) | |
| *C08K 3/22* | (2006.01) | |
| *C07C 31/22* | (2006.01) | |
| *C07C 31/26* | (2006.01) | |
| *C07H 3/04* | (2006.01) | |
| *C08G 65/34* | (2006.01) | |
| *C08L 89/00* | (2006.01) | |

(52) U.S. Cl.
CPC ........ *C07K 14/4732* (2013.01); *C07C 31/225* (2013.01); *C07C 31/26* (2013.01); *C07H 3/04* (2013.01); *C08G 65/34* (2013.01); *C08J 5/18* (2013.01); *C08K 3/22* (2013.01); *C08K 5/053* (2013.01); *C08L 89/00* (2013.01); *C08J 2389/00* (2013.01); *C08K 2003/2206* (2013.01); *C08L 2666/68* (2013.01)

(58) Field of Classification Search
CPC ...... C07K 14/4732; C07H 3/04; C08G 65/34; C08L 2666/68; C08L 89/00
USPC ........................................................ 426/138
See application file for complete search history.

(56) References Cited

U.S. PATENT DOCUMENTS

| 6,379,726 B1 | 4/2002 | Tomasula |
| 2010/0063110 A1 | 3/2010 | Meyer et al. |

FOREIGN PATENT DOCUMENTS

| CN | 105176102 A1 | 12/2015 |
| EP | 0547551 A1 | 6/1993 |
| WO | 2004035029 A1 | 4/2004 |

OTHER PUBLICATIONS

International Searching Authority, PCT/US2017/047491 for The United States of America, as Represented by the Secretary of Agriculture et al., International Filing Date Aug. 18, 2017.
Folegatti et al., "Mechanical and Permeability Properties of Milk Protein Films," UNICAMP—Faculdade de Engenharia de Alimentos, C.P. 6017-CEP 13083-970. Campinas-S.P.Brasil., 2 San Jose,State University, CA, USA Abstract.
Bonnaillie et al., "Application of Humidity-Controlled Dynamic Mechanical Analysis (DMA-RH) to Moisture-Sensitive Edible Casein Films for Use in Food Packaging," Polymers, (2015) 7:91-114.
Bonnaillie et al., "Casein Films: The Effects of Formulation, Environmental Conditions and the Addition of Citric Pectin on the Structure and Mechanical Properties," Polymers, (2014) 6:2018-2036.

*Primary Examiner* — Jyoti Chawla
(74) *Attorney, Agent, or Firm* — John D. Fado; Ariel L. Atkinson

(57) ABSTRACT

Improved casein-based films are produced by adjusting the pH of a film-production suspension. The film-production suspension may contain a casein source, a plasticizer, and optionally a strengthening additive. The adjustment of the pH may be accomplished by the addition of an alkaline additive, such as a base, to achieve a desired pH value. The improved casein-based films have improved physical properties as compared to those produced without a pH-adjusted film-production suspension at least in part due to the chemical and structural changes imparted by the change in pH.

24 Claims, 12 Drawing Sheets
(7 of 12 Drawing Sheet(s) Filed in Color)

| pH | NFDM/Gly | NFDM/CaCN/Gly |
|---|---|---|
| 7 |  opaque and brittle, with a coarse crystalline structure |  hazy, with large areas of lactose crystals |
| 9 |  opaque and more pliable, finer crystalline structure |  clear, with smaller and more disperse crystals |
| 11 |  clear, flexible, and stretchy |  very clear, smooth, very small and dispersed crystals |

ALKALINE PH-MODIFIED EDIBLE CASEIN-BASED FILMS AND COATINGS, AND METHOD FOR THE MAKING THEREOF

REFERENCE TO RELATED APPLICATIONS

This application claims the benefit of U.S. Provisional Application No. 62/377,288 filed Aug. 19, 2016 which is incorporated herein by reference in its entirety.

BACKGROUND

This invention relates to improved edible films and coatings manufactured from casein and caseinates. The invention specifically relates to improving these films by addition of an alkaline additive.

Casein protein is the principal solid constituent of milk. "Casein" refers to a group of phosphoproteins possessing intermolecular surface activity which enables the proteins to form a micelle structure in milk. This surface activity is based on a variety of functional groups and complex charge distribution. In turn, these functional groups and charges distributed over the casein molecule influence intra-molecular interactions and the folding/unfolding of the protein. Casein can be separated from milk by lowering the pH to a threshold of about 4.6, below which casein precipitates in a form known as acid casein.

Casein can be combined with other materials to form an edible material that can be shaped into, for instance, thin films that can be used in food packaging and coatings. U.S. Pat. No. 6,379,726 to Tomasula, which is incorporated herein by reference in its entirety, discloses a method for preparing such water-insoluble protein-based edible films and coatings from casein that exhibit improved water-solubility resistance and barrier and mechanical properties. Edible films from micellar casein or a commercial calcium caseinate (CaCN or CaCas) and glycerol (Gly) as a plasticizer in a 3:1 ratio are strong in normal environmental conditions (20 degrees C. and 50% relative humidity (RH)) but are hydrophilic and begin to lose their integrity above 60% RH or 35 degrees C. which greatly limits their usefulness for films.

The current inventors demonstrated the use of humidity-controlled dynamic mechanical analysis (DMA-RH) to precisely identify the effects of temperature and relative humidity on CaCN/Gly films over the entire range of environmental conditions that may be found during the fabrication, distribution, storage and utilization of edible casein films. CaCN/Gly films were found within a matter of weeks to become more brittle, and 1-2 week old films demonstrated several transitions in the structure of the polymeric network at different sets of temperature and relative humidity with good repeatability.

It would be useful to improve on the casein film to produce a more robust application. It is well known that the different types of caseins that form casein micelles ($\beta$-CN, $\alpha_{s1}$-CN, $\alpha_{s2}$-CN and $\kappa$-CN, in ratios of 4:4:1:1) become unstable at acidic pH and collectively precipitate at pH ~4.6. However, few studies, if any, exist relating to the effect on caseinates or casein-based protein films when increasing the pH over 7.

All of the references cited herein, including U.S. Patents and U.S. Patent Application Publications, are incorporated by reference in their entirety.

Mention of trade names or commercial products in this publication is solely for the purpose of providing specific information and does not imply recommendation or endorsement by the U.S. Department of Agriculture.

SUMMARY

Improved casein-based films and coatings may be produced by adjusting the pH of a film-production suspension by the addition of an alkaline additive. The film-production suspension may contain a casein source, a plasticizer, and optionally a strengthening additive. The adjustment of the pH may be accomplished by the addition of an alkaline additive, such as a base, to achieve a desired pH value. The improved casein-based films may have improved physical properties as compared to those produced without a pH-adjusted film-production suspension at least in part due to the chemical and structural changes imparted by the change in pH and the introduction of a different cations.

According to at least one exemplary embodiment of the invention, a casein-based film may include a casein source, a plasticizer, and an alkaline additive, and the film may have a melting point temperature at 50% relative humidity of at least 60° C.

According to a further aspect of the invention, the casein-based film may have a storage modulus, G', at 50% relative humidity and 60° C., of at least 150 MPa.

According to a further aspect of the invention, the casein source may be one of a caseinate, a fluid or dried milk product, milk protein concentrate, micellar casein concentrate, and a mixture thereof.

According to a further aspect, the plasticizer may be one of glycerol, sorbitol, propylene glycol, polypropylene glycol, sucrose, and a mixture thereof.

According to yet a further aspect, the casein source and the plasticizer may be present in a ratio of casein source: plasticizer of 99:1 to 1:1.

According to yet a further aspect, the casein-based film may also include a strengthening additive.

According to yet a further aspect, the strengthening additive may be one of a pectin, a polysaccharide, a pullulan-microbial polysaccharide, a dextrin, an oligosaccharides, a monosaccharide, a disaccharide, high fructose corn syrup, cellulose, hemi-cellulose, a gum or the constitutive sugar thereof, methylcarboxycellulose, gelatin, carrageenan, agar, an alginates, egg albumen, transglutaminase, tyrosinase, an aglycone, a glycoside, a chloride salt, a bicarbonates, a phosphate, one of vitamins A-K, milk fat, a polyunsaturated fat, a monosaturated fat, an omega-3 fatty acid, a conjugated linolenic acid, alpha linolenic acid, a phospholipid from milkfat, a lecithin, a sterol, soluble or insoluble plant fiber, a fiber gum, psyllium, flax seed, quince seed, an antioxidant, a carotenoid, and a mixture thereof.

According to yet a further aspect, the strengthening additive may be present in an amount of 0.05% to 5% (w/w).

According to another aspect of the invention, a method for producing a casein-based film may include producing a film-production suspension, the film-production suspension comprising a solvent, a casein source, and a plasticizer, adjusting the pH of the film-production solution to at least ≥8.0, creating a film from the pH-adjusted film-production suspension by drying, and thereby obtaining a casein-based film.

According to a further aspect, the solvent may be water.

According to yet a further aspect, the producing of the film-production suspension may be performed by either: (i) adding the plasticizer to the solvent to create a solvent-plasticizer suspension, then adding the casein source to the plasticizer-solvent suspension to create a solvent-plasticizercasein suspension, then adding the strengthening additive to create the film-production suspension; (ii) adding the plasticizer to the solvent to create a solvent-plasticizer suspension, then adding the strengthening additive to create a solvent-plasticizer-strengthening additive suspension, then adding the casein source to the solvent-plasticizer-strengthening additive suspension to create the film-production suspension; or (iii) adding the strengthening additive to the solvent to create a solvent-strengthening additive suspension, then adding the casein source to the solvent-strengthening additive suspension to create a solvent-strengthening additive-casein suspension, then adding the plasticizer to the solvent-strengthening additive-casein suspension to create the film-production suspension.

According to yet a further aspect, the adjusting the pH of the film-production suspension may include adding an alkaline additive to the film-production suspension.

According to yet a further aspect, the alkaline additive may be one of a monovalent hydroxide, a divalent hydroxide, and ammonium.

According to yet a further aspect, the adjusting the pH of the film-production suspension may include adjusting the pH to at least ≥8.5.

According to yet a further aspect, the adjusting the pH of the film-production suspension may include adjusting the pH to at least ≥9.0.

According to yet a further aspect, the adjusting the pH of the film-production suspension may include adjusting the pH to at least ≥9.4.

According to yet a further aspect, the adjusting the pH of the film-production suspension may include adjusting the pH to a value of about 8.5 to about 12.0.

According to yet a further aspect, the creating of the film from the pH-adjusted film-production suspension by drying may include one of casting a film in mold, spraying, and dipping.

BRIEF DESCRIPTION OF THE FIGURES

The patent or application file contains at least one drawing executed in color. Copies of this patent or patent application publication with color drawing(s) will be provided by the Office upon request and payment of the necessary fee.

Advantages of embodiments of the present invention will be apparent from the following detailed description of the exemplary embodiments. The following detailed description should be considered in conjunction with the accompanying figures in which.

Exemplary

Exemplary

Exemplary

Exemplary

Exemplary

Exemplary

Exemplary

Exemplary

Exemplary

Exemplary

Exemplary

Exemplary

Exemplary

Exemplary

Exemplary

Exemplary

Exemplary

Exemplary

Exemplary

Exemplary

Exemplary

Exemplary

DETAILED DESCRIPTION

Figure 1A:
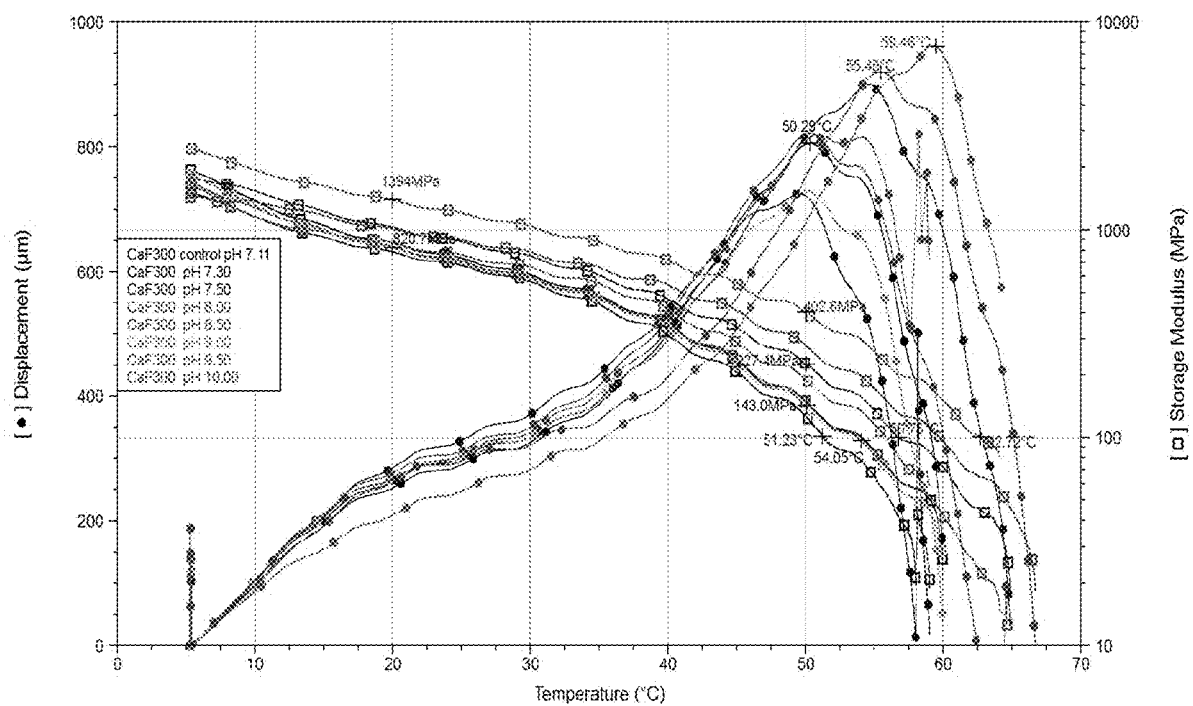
FIG. 1A shows measurements of storage modulus (E', MPa) and displacement as a function of temperature for films according to the present invention.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description, discussion of several terms used herein follows.

As used herein, the word "exemplary" means "serving as an example, instance or illustration." The embodiments described herein are not limiting, but rather are exemplary only. It should be understood that the described embodiment are not necessarily to be construed as preferred or advantageous over other embodiments. Moreover, the terms "embodiments of the invention", "embodiments" or "invention" do not require that all embodiments of the invention include the discussed feature, advantage or mode of operation.

"Optional" or "optionally" means that the subsequently described event or circumstance may or may not occur, and that the description includes instances in which said event or circumstance occurs and instances where it does not. For example, the phrase "optionally comprising X" means that the composition may or may not contain X, and that this description includes compositions that contain and do not contain X.

The term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

Unless defined otherwise, all technical and scientific terms used herein have the same meaning as commonly understood by one of ordinary skill in the art to which the invention belongs. As used herein, the term "about" refers to a quantity, level, value, or amount that varies by as much as 30%, preferably by as much as 20%, and more preferably by as much as 10% to a reference quantity, level, value, or amount. Although any methods and materials similar or equivalent to those described herein can be used in the practice or testing of the present invention, the preferred methods and materials are now described.

The term "consisting essentially of," as may be used herein, excludes additional method steps or composition components that substantially interfere with the intended activity of the method or composition, and can be readily determined by those skilled in the art, for example, from a consideration of this specification or practice of the invention disclosed herein.

The invention illustratively disclosed herein suitably may be practiced in the absence of any element (e.g., method steps or composition components) which is not specifically disclosed herein.

The amounts, percentages, and ranges disclosed herein are not meant to be limiting unless otherwise specified, and increments between the recited amounts, percentages, and ranges are specifically envisioned as part of the invention.

Exemplary Method for Producing Casein-Based Films

Casein-based films were produced using the following process: a casein source, such as calcium caseinate, was combined with a plasticizer, such as glycerol, in a solvent to create a film-production suspension. A film-production suspension may be produced by first mixing the plasticizer, such as glycerol, with distilled water for 30 minutes and then adding the casein source, such as calcium caseinate powder, and mixing via a magnetic stir bar at 500 rpm for 120 minutes. Each suspension may contain about 15% (w/w) total solids, with the ratio of caseinate:glycerol being set to a particular value, for example 3:1. Each suspension may then be unmodified (control, with an initial pH of about 6.7 to 7.1) or the pH may then be adjusted by the addition of an alkaline additive, such as sodium hydroxide (NaOH), at either 0.1N or 1N concentration to obtain a target pH value. Alternatively, the alkaline additive may be added at other concentrations, such as 0.05N, 0.5N, or as desired, to obtain the target pH value. The target pH value is always alkaline. In some embodiments, the target pH may be at least 8.0. According to some embodiments, the pH may be preferably between 8.5 and 12.0, and more preferably between 9.0 and 10.0. According to some embodiments, the pH may be preferably about 8.4-8.6, and according to at least some other embodiments, the pH may be about 9.4-9.7. According to at least one embodiment, the preferred pH may depend on the components of the suspension, such as which alkaline additive is used to create a basic environment. Alkaline additives which may be used in the present invention include, but are not limited to, sodium hydroxide (NaOH), calcium hydroxide ($Ca(OH)_2$), another monovalent or divalent hydroxide, or any other alkaline hydroxide, or ammonium.

In addition to the above components, a strengthening additive may be added to the film-production suspension prior to creating a film therefrom. The strengthening additive may be, for example, a pectin such as citric pectin. Other examples of a strengthening additive may include, but are not limited to polysaccharides (such as starches); pullulan-microbial polysaccharides; dextrins; oligosaccharides, such as galacto-oligosaccharaides and fructooligosaccharides; monosaccharides and disaccharides, such as such as glucose, sucrose, fructose, lactose, and galactose; high fructose corn syrup; celluloses; hemi-celluloses; gums, such as guar and locust bean, konjac, xanthan, Arabic, gellan, and their constitutive sugars; methylcarboxycellulose; gelatin; carrageenans, agar, alginates, and other algae derivatives; proteins such as egg albumen, plant proteins such as soy or almond, e.g., bioactive peptides from proteins, amino acids, and enzymes such as transglutaminase, tyrosinase, aglycones such as genipin, and glycosides such as oleuropein; salts such as calcium, sodium, potassium, and magnesium as chlorides; bicarbonates; phosphates, e.g., singly or from a waste stream such as ultrafiltration or microfiltration permeates; vitamins A-K; fats such as milk fats, fatty acids such as the polyunsaturated fats, monosaturated fats, healthy fats such as omega-3 fatty acids, conjugated linolenic acids (CLA), EPA, DHA, alpha linolenic acid (ALA), phospholipids from milkfat, and lecithins; sterols such as the plant sterols, etc; such fibers from those plants, including soluble and insoluble fibers, and fiber gums; seeds such as psyllium, flax seed, and quince seed; antioxidants such as the polyphenols, which include quercetin, etc.; carotenoids such as lutein and lycopene; and mixtures thereof. The strengthening additive may be present in an amount so as to not negatively affect the properties of the film, for example 0.05% to 5% (w/w) of the dried film.

Films were cast using the method of Bonnaillie et al. (Bonnaillie, L. M.; Zhang, H.; Akkurt, S.; Yam, K. L.; Tomasula, P. M., Casein Films: The Effects of Formulation, Environmental Conditions and the Addition of Citric Pectin on the Structure and Mechanical Properties *Polymers* 2014, 6, 2018-2036), which is incorporated herein by reference in its entirety. Approximately 20 mL of suspension was spread evenly onto a silicon baking mat (Weston Products LLC., Strongsville, Ohio) with a K-101 Control Coater apparatus (RK Print-Coat Instruments Ltd., Royston, UK), using spreading speed #3 and spreader bar #300, to produce rectangular films of approximately 15 cm×25 cm and 0.03-0.05 mm thickness (average of 0.040 mm). The edges of each film were allowed to set for 1-2 hour in uncontrolled atmospheric conditions in the laboratory, then the silicon mats were transferred to an environmental chamber (Model 6020-1, Caron, Marietta, Ohio) set to 20° C. and 50% RH to finish drying in constant conditions. The films were peeled after 24 h, then placed between sheets of paper and stored in the chamber for 7 days before beginning testing. The dried films had a composition of about 75% caseinate and 25% Gly (plus moisture and any additives, as described).

It is understood the film of the present invention may be produced by a casting method, such as that described above, as well as by spraying, dipping, brushing, panning, or any other known method of creating a film from a liquid suspension. Further, the "film" of the present invention includes a film material which may be "stand-alone," combined with other elements to make a product, such as a bag or container, or a coating, such as on a food product.

It is understood that variations may be made to the above exemplary method and achieve the same or similar results. For example, the casein source of the above method may be sodium caseinate, dried or powdered milk, or other chemical forms of casein. Examples of casein sources envisioned in the present invention include all caseinates, fluid and dried milk products, milk protein concentrates, micellar casein concentrates, and a mixtures thereof. Further, a plasticizer other than glycerol may be used, such as sorbitol, propylene glycol, polypropylene glycol, sucrose, and mixtures thereof, or others known in the art. In addition, various bases may be used to adjust the alkalinity of the suspension to a desired level. Further, the percentage of solids in the suspension may vary from about 3% to about 30% (w/w). At higher solids amounts in the suspension, the addition of heat to suspension may be necessary to lower the viscosity sufficiently to produce a film. Even further, the ratio of the casein source to the plasticizer may vary from about 100:0 to about 1:1. Hence, the composition of the dried films may thus range, from about 100% casein source to about 50% casein source (and thus about 0% plasticizer to about 50% plasticizer). It is preferred that the components in the film-production suspension, and thus the dried films, are present in an amount that would not cause harmful health effects if ingested, which is to say, it is preferable that the components of, and thus the entirety of, the dried film be edible.

Other modifications of this method may be set out in the Examples below.

Testing and Characterization

Microscopic Imaging. The surface appearance of the films was recorded using an optical LEICA MZ FL III microscope with Intralux® 5000-1 (Leica Microsystems Inc., Buffalo Grove, Ill.), equipped with the LAS v. 3.8 (Leica Application Suite) software and a DFC 420 C Twain Version 7.7.1.0 camera (also Leica). Film areas of 1 mm×0.75 mm were magnified 4× to 20× and digital images were captured in black and white. The brightness and contrast of the images were adjusted for clarity.

Tensile Testing. A Burst Test fixture with five 10 mm diameter wells (TA-1085-5i indexing film testing fixture, Texture Technologies Corp., Scarsdale, N.Y.) was chosen to measure the tensile properties of the films. A 30 mm×150 mm film strip was placed over the fixture and the position of the 5 wells marked, then the thickness of the film was averaged at 5 different locations for each of the 5 wells. The film strip was then secured tightly over the 5 wells with a top-plate and the fixture inserted into a TAXT2i Texture Analyzer (Texture Technologies Corp., Scarsdale, N.Y.). A 5 mm steel ball-probe descended through each disc-shape sample at a rate of 0.10 or 0.5 mm/s (depending on the film series), progressively stretched it, and finally burst it. The initial trigger force was set to 5 g. The Exponent Software recorded the force as a function of distance covered by the probe and the curves were similar to traditional stress-strain curves using ASTM D882. The results for the initial slope (S, in N/mm), force at break (F, in N) and distance at break (D, in mm) were recorded for each sample, then normalized by dividing by the thickness. Environmental conditions during the tests were ~23° C. and 50% RH, as controlled by a custom environmental chamber (ETS, Glenside, Pa.). Films were equilibrated in the chamber for at least 1 hour before testing.

Humidity-Controlled Dynamic Mechanical Analysis. A DMA Q800 with an RH-attachment (both TA Instruments) was employed to measure the dynamic tensile properties of films under broad environmental conditions, using the detailed methodology of Bonnaillie et al. (Bonnaillie, L. M.; Tomasula, P. M., Application of humidity-controlled dynamic mechanical analysis (DMA-RH) to moisture-sensitive edible casein films for use in food packaging. *Polymers* 2015, 7, 91-114); the instrument is also described in detail therein. A 0.1% (15 μm) oscillatory strain was applied to 15 mm×5 mm×0.040 mm film strips mounted onto a tensile clamp, with a frequency of 4 Hz. A pre-load force of 0.2 N and the "force track" option were selected, to prevent any slack in the film strips. During each oscillation, the Advantage for Q Series Version software (Thermal Advantage Release 5.2.6, TA Instruments) recorded the input strain, the resulting stress, and the lag between the two (the phase angle $\delta$), then calculated the following values:

The Storage Modulus, E' (MPa)=stress/strain×cos $\delta$, is the ability of the film to store energy and represents its elastic properties (E' is similar to the stiffness). It is often schematized with a spring;

The Loss Modulus, E" (MPa)=stress/strain×sin $\delta$, is the heat dissipated by the film as a result of molecular motions (damping), and represents the viscous properties. It is usually schematized with a piston;

The complex modulus: E*=E'+iE", is the film's resistance to deformation; and

Tan $\delta$=E"/E', is the ratio of the dissipated energy to the energy stored per oscillation and characterizes the film's damping properties. For purely elastic materials, Tan $\delta$=0; for pure liquids, Tan $\delta$=∞ (i.e., $\delta$=90°); visco-elastic materials display intermediate values.

After mounting, film samples were measured with the software then equilibrated at 5° C. and 50% RH for 120 min, then subjected to a temperature ramp from 5° C. to 90° C. (rate of 0.1 or 0.33° C./min) at 50% RH.

It is noted that the above mechanical testing may also reveal the melting point temperature of a sample.

Liquid Rheology. The properties of the suspensions at 25° C. in transient and oscillatory modes were tested with an AR2000 dynamic rheometer (TA Instruments, New Castle, Del.) with a Couette attachment and Peltier heater and a 2-step program: transient behavior was measured with a stress-sweep from 10 to 1000 s$^{-1}$ in continuous flow; followed by oscillations at 30% strain with a frequency sweep from 0.6 to 60 rad/s.

Solubility. One inch by one inch (1"×1") squares of films were cut with scissors, then deposited with tweezers on the surface of a pan of still distilled water at 23° C. A timer was started upon deposition of the films, then the films were visually or photographically monitored as a function of time to record swelling, breakage, and dissolution behaviors.

Example 1: Casein-Based pH-Adjusted Films

Films with coarsely-adjusted pH. Films were produced according to the method described above. Suspensions of CaCN/Gly (3:1 CaCN:Gly, 15% (w/w) total solids) had their pH coarsely adjusted between approximately 7 (control, actual pH 7.11) up to a pH of 10, and films were cast from the control and pH-adjusted suspensions.

Figure 1B:
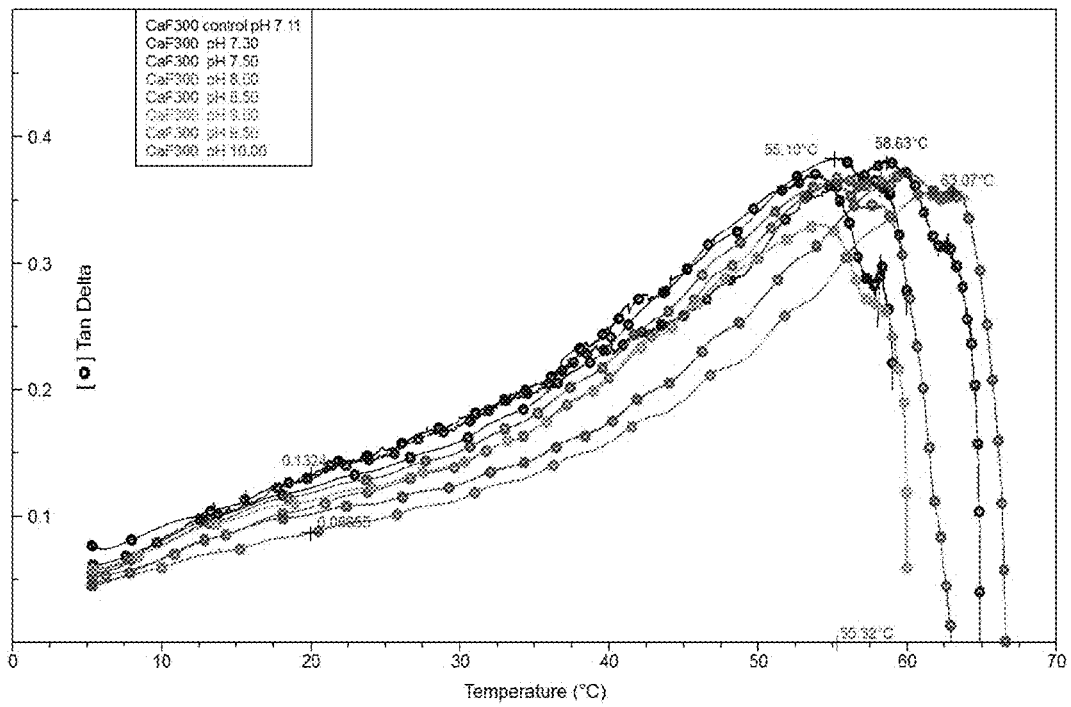
FIG. 1B shows measurement of tan δ (tan delta), which characterizes a film's damping properties, for films according to the present invention.

The results of mechanical testing of the resulting films are shown in FIG. 1A and FIG. 1B. The figures show that, relative to the control, the films cast from pH 7.5-8.5 have a slight improvement in strength. The strength at a pH of 9.0 suddenly drops, and then becomes remarkably better at 9.5, before decreasing again at pH of 10.

Films with finely-adjusted pH. Films were produced according to the same method above, except that pH was finely adjusted between 9.0 and 10.0 to determine the pH with the optimal melting temperature. The results are shown in Table 1 below:

TABLE 1

Melting temperatures of Ca/CN films made at different pHs.

| pH | Average Melting Temperature |
|---|---|
| 7 (control) | 50° C. |
| 9.0 | 50° C. |
| 9.1 | 54.5° C. |
| 9.2 | 60° C. |
| 9.3 | 60° C. |
| 9.4 | 60° C. |
| 9.5 | 60° C. |
| 9.6 | 60.5° C. |
| 9.7 | 59° C. |
| 10.0 | 55° C. |

As seen in Table 1 above, the maximum melting point temperature found for these films was for films made at a pH of 9.6. Of note is that the melting point temperature increased by a little over 10° C. from the control to the maximum point.

Figure 2:
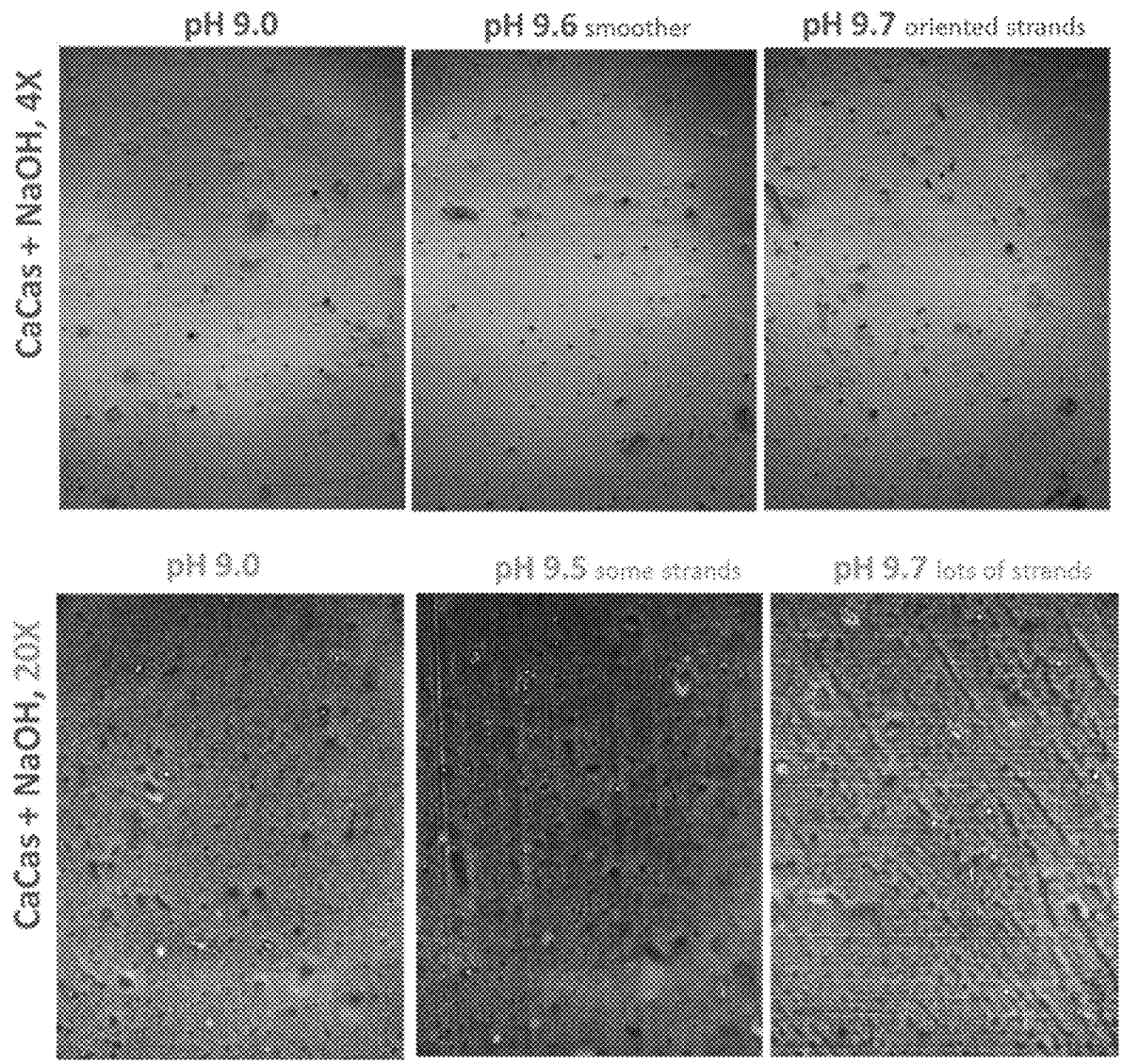
FIG. 2 shows micrographs at 4× and 20× magnification of films according to the present invention.

In addition to melting point temperature, optical micrographs were taken of the films to determine the differences in structure. FIG. 2 shows micrographs of films made from suspensions at a pH of 9.0, 9.6, and 9.7, at both 4× and 20× magnifications. Of note are the strands that form at higher pHs, which are somewhat evident in the pH 9.6 sample and much more prevalent in the pH 9.7 sample. As pH increases, CaCN molecules become more and more linear and thus form these longer strands. In addition, viscosity increases with the friction formed by these strands, causing alignment "memory" in the dry films above pH 9.4.

Figure 3A:
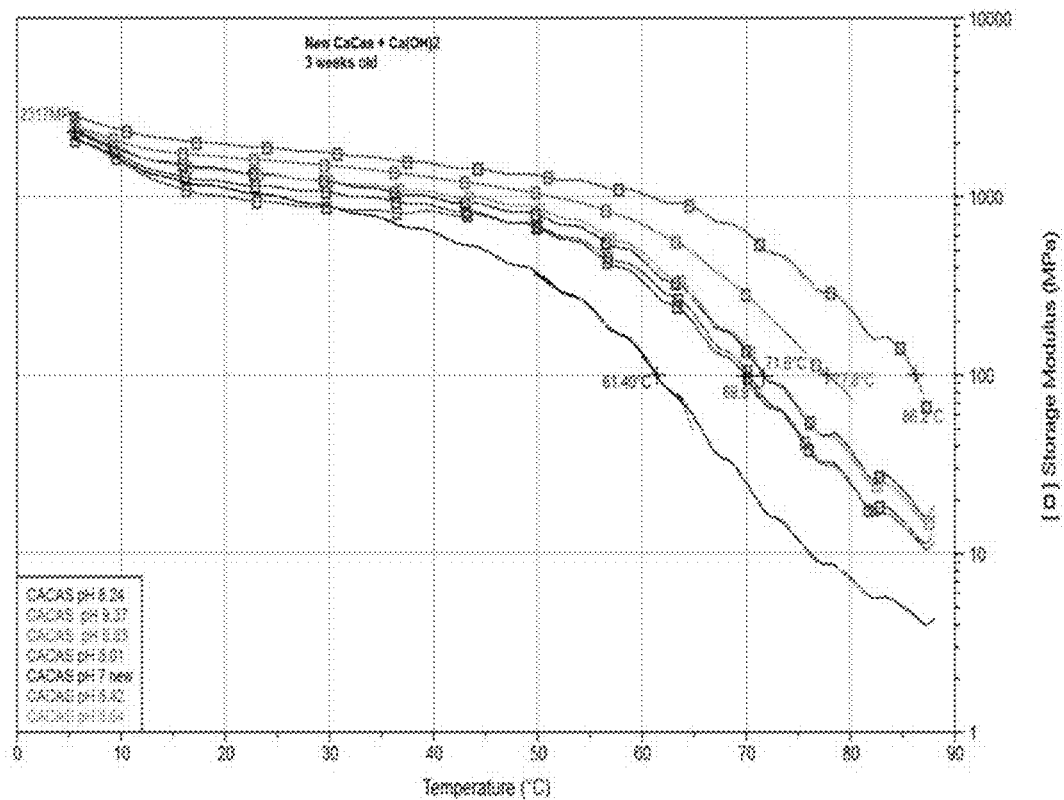
FIG. 3A shows measurements of storage modulus (E', MPa) as a function of temperature for films according to the present invention.
Figure 3B:
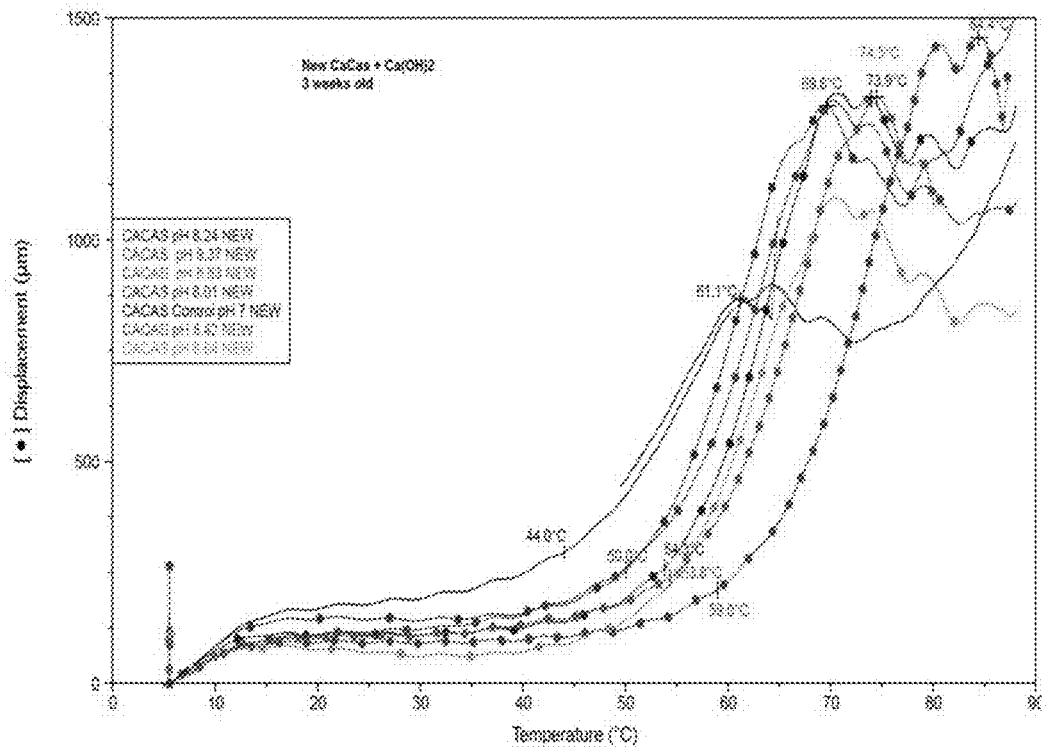
FIG. 3B shows measurements of displacement as a function of temperature for films according to the present invention.

Films with calcium hydroxide ($Ca(OH)_2$). In a variation of the above method, films were made with $Ca(OH)_2$ as the alkaline additive instead of NaOH. The pH of the suspension was raised using $Ca(OH)_2$ to a level between 8.0 and 9.4. Above a pH of 9.4, the suspension would become very viscous and be difficult to cast. The results of mechanical tests on the resulting films, including an unmodified control, are shown in FIG. 3A and FIG. 3B. In particular, films formed from a suspension at a pH of 9.37 showed the strongest mechanical properties. Of note is that though the mechanical properties increase from a pH of 7 to 8.01 to 8.24, when raised above that to 8.42, there is a setback until the strength jumps up significantly at a pH of 8.83, and then continues to increase with a pH of 9.37. Thus this localized minimum, observed with NaOH at a pH of about 9.0 also shows up in suspensions with $Ca(OH)_2$, only at a lower pH.

Example 2: Rheology of Casein-Based Suspensions

Rheology studies were undertaken to further elucidate the mechanism for the improved properties found at a certain pH level.

Figures 4A, 4B:
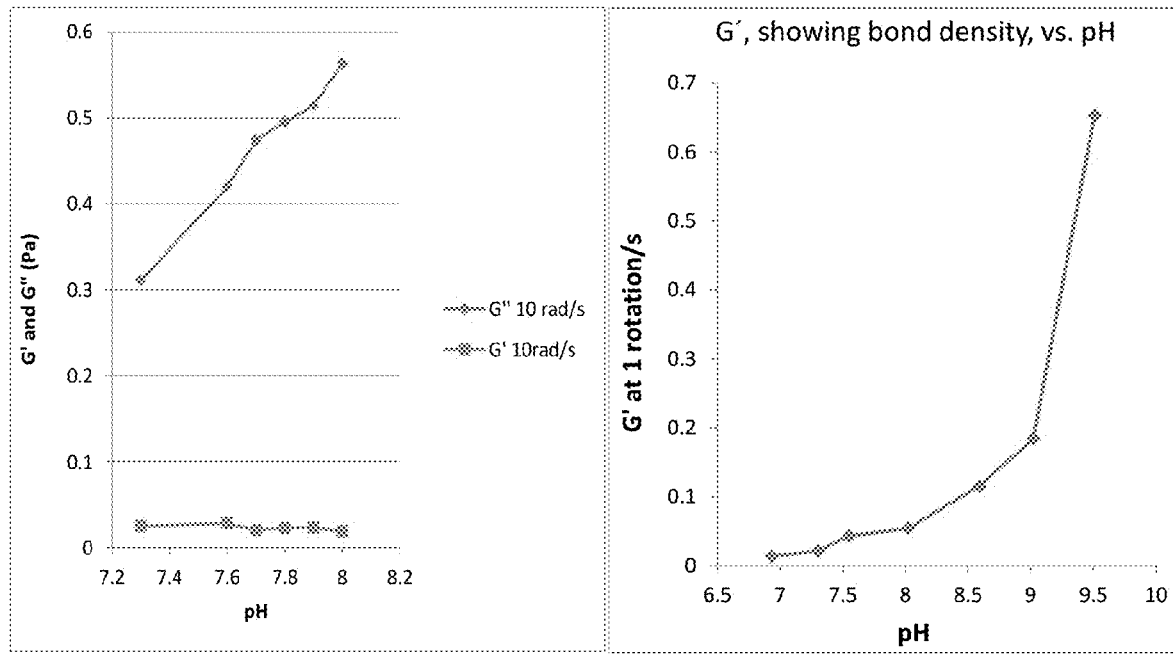
FIG. 4A shows the results of an oscillation study (30% strain and 10 rad/s) of CaCN/Gly (3:1) suspensions at 25° C. as a function of pH with NaOH as the alkaline additive.
FIG. 4B shows the results of frequency sweeps at 1 rotation/s of the same type of suspension as in FIG. 4A at 20° C. and from pH 6.9 to 9.5.
Figure 4C:
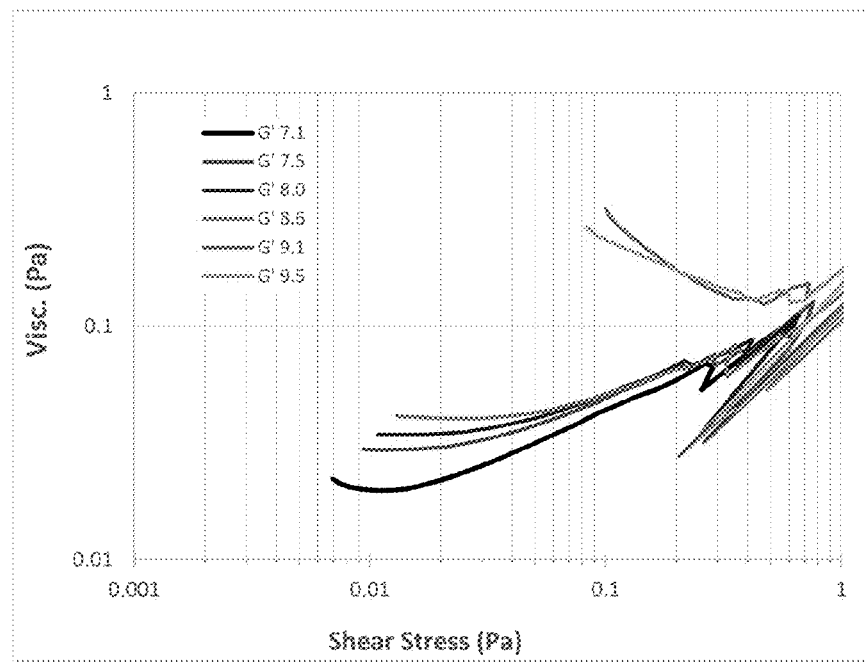
FIG. 4C shows the results of frequency sweeps of the same suspension as in FIG. 4A at 25° C. between pH 7.1 and 9.5.

Rheology of CaCN suspensions with NaOH. In a first study, the elastic modulus (G') and viscous modulus (G") were evaluated on suspensions prepared according to the above method, using CaCN and glycerol, and at various pHs, the pH being modified by addition of NaOH. The results of these studies are shown in FIG. 4A and FIG. 4B. Further, the shear viscosity vs. shear stress was determined for several samples, the results of which are shown in FIG. 4C. By combining this data, it can be seen that there is a non-linear relationship between pH and the suspension's physical properties, including a sharp change between a pH of 9.0 and 9.5 (FIG. 4B) and also between a pH of 8.6 and 9.1 (FIG. 4C). Such results show that a significant change in the structure of the suspension occurs between a pH of 9.0 and 9.1, at least for the compositions tested. In particular, the CaCN/Gly suspension is shear-thickening at a pH of ≤8.6, and then suddenly becomes a shear-thinning gel between pH values of 9.0 and 9.1.

Figure 5A:
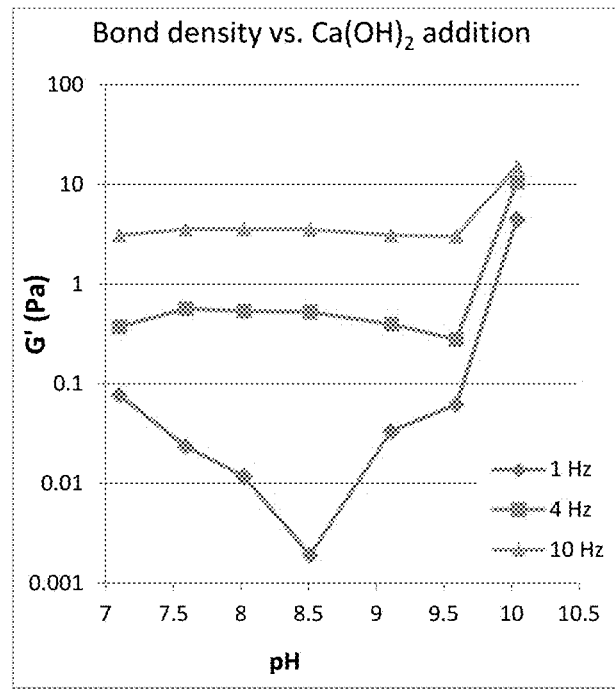
FIG. 5A shows the results of frequency sweeps at 1, 4, and 10 Hz of CaCN/Gly (3:1) suspensions at 25° C. as a function of pH with $Ca(OH)_2$ as the alkaline additive.
Figure 5B:
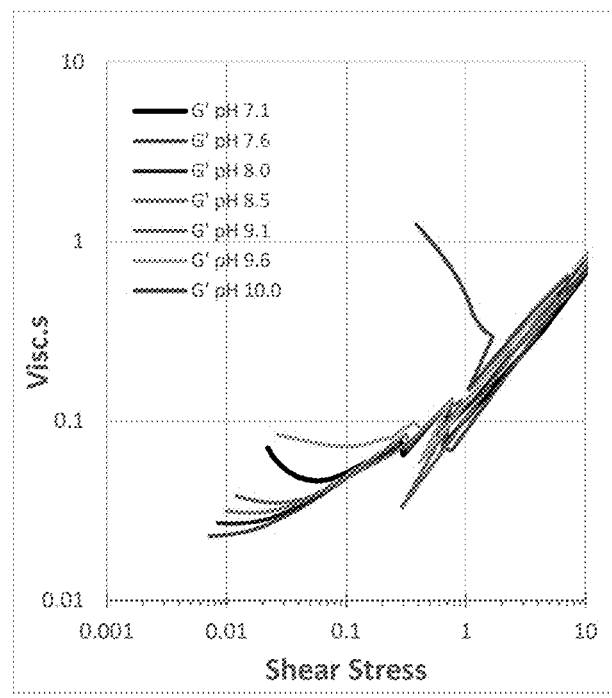
FIG. 5B shows the results of frequency sweeps of the same suspension as in FIG. 5A at 25° C. between pH 7.6 and 9.1.

Rheology of CaCN suspensions with $Ca(OH)_2$. The above rheology experiment was repeated with $Ca(OH)_2$ instead of NaOH. The corresponding results of testing the properties of the new suspensions are shown in FIG. 5A and FIG. 5B. In a similar analysis as was applied above, here the significant "jump" in the physical properties of the suspension occurs between the pH values of 9.6 and 10.

Figure 6:
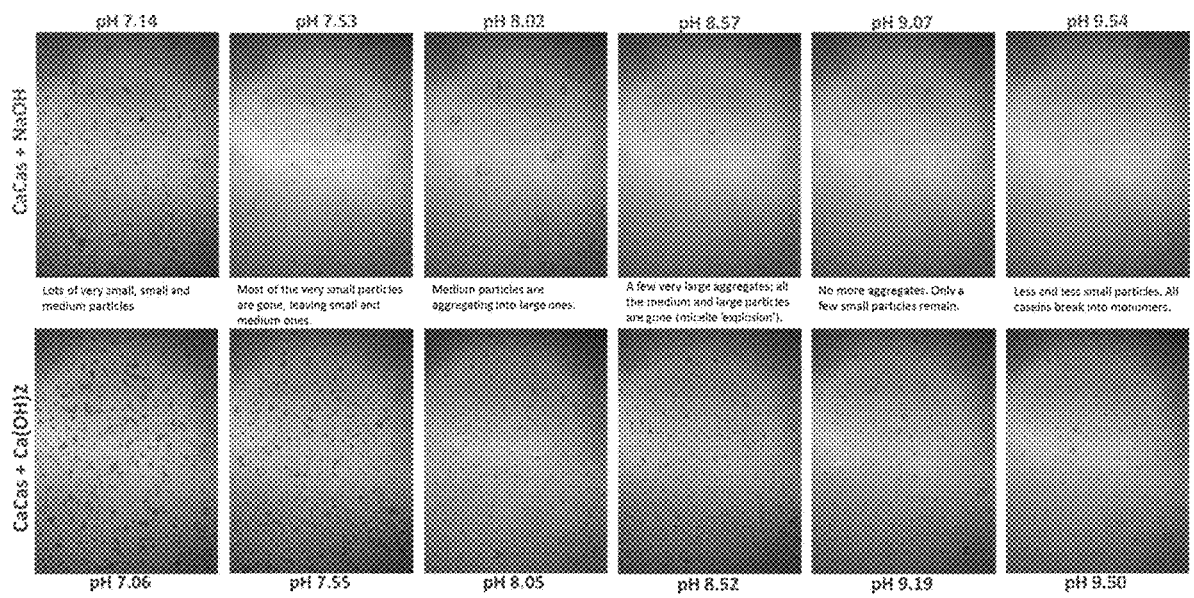
FIG. 6 shows micrographs of suspensions with either NaOH or $Ca(OH)_2$ as the alkaline additive from a pH of about 7 to about 9.5.

NaOH vs. $Ca(OH)_2$ suspension microscopy. Suspensions were prepared using both NaOH and $Ca(OH)_2$ to approximately the same pH values and micrographs taken to directly compare the two alkaline additives. The images are shown in FIG. 6. Because it was exceedingly difficult to adjust the samples to the exact same pH values, the exact (measured) pH of each sample is given. In particular, and consistent with the above rheology results, the NaOH samples show no more aggregates starting between pHs of 9.0 and 9.1 (at 9.07). Further, consistent with the above results, the $Ca(OH)_2$ sample at a pH of 9.50, though noticeably clearer than lower pHs, still has a significant number of particles which are absent in the NaOH sample at almost the same pH (9.54). It is expected that if the pH of the $Ca(OH)_2$ sample were raised to above 9.6, it would look similar to the NaOH sample at 9.54, though this data is not shown.

The combination of the rheology and microscopy studies indicate that a structural change takes place above a certain threshold pH value, and that the threshold pH value is dependent on at least the alkaline additive chosen.

Example 3: Embodiments Using a Strengthening Additive

As disclosed previously, a strengthening additive, such as citric pectin, can be added to caseinate suspensions to assist in the formation of films (Bonnaillie et al. 2014). Further, the same paper discussed the differences in the order of addition of the reagents to create the suspension and how such an order can affect the resulting properties. The present inventors opted to apply the findings supra regarding pH adjustment to different formulations made by changing the order of addition of the reagents to determine how pH affected those formulations. The pectin used was a citric pectin (CP).

The pectin was first dissolved to make a concentrated solution, and then added to the suspension according to the particular formulation method being used. The final amount of pectin in the dried films for which pectin has been added can range from 0.05% to 5%. In particular, the formulations used herein are given in Table 2 below:

TABLE 2

Formulations used in Example 3

| Formulation | Corresponding formulation in Bonnaillie et at. 2014 | Order of addition of reagents |
|---|---|---|
| (A) | E | 1. Water + glycerol<br>2. Calcium caseinate<br>3. Pectin |
| (B) | F | 1. Water + glycerol<br>2. Pectin<br>3. Calcium caseinate |
| (C) | G | 1. Water + pectin<br>2. Calcium caseinate<br>3. Glycerol |

Figure 7A:
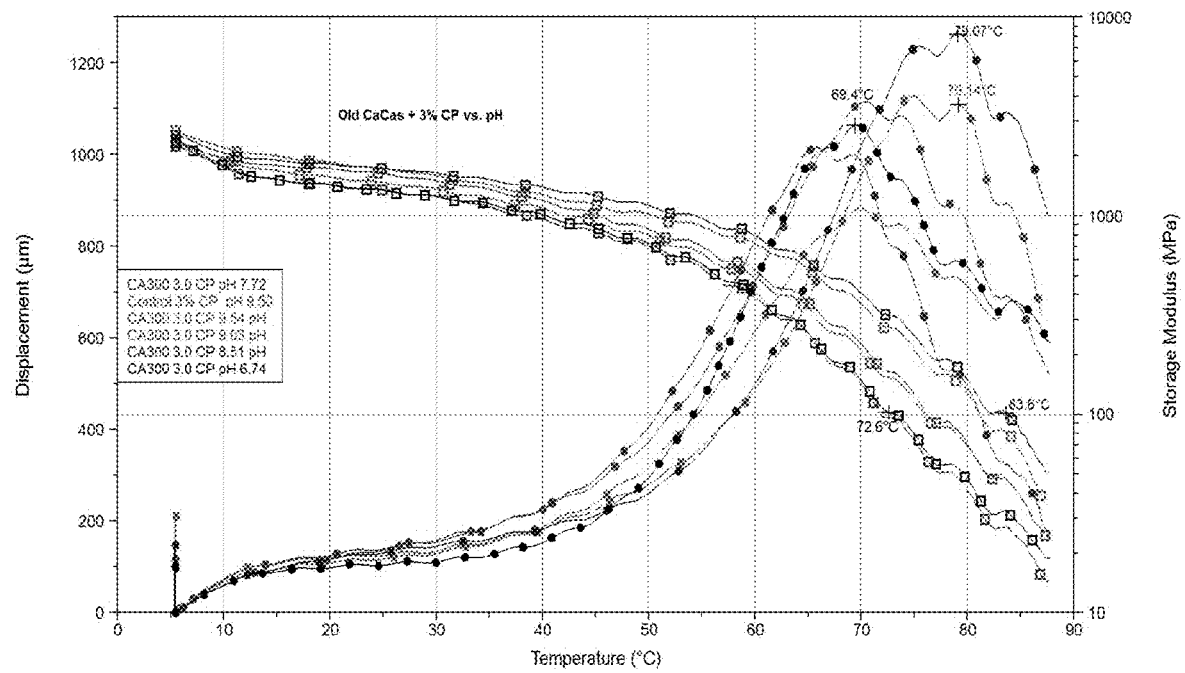
FIG. 7A shows measurements of storage modulus (E', MPa) and displacement as a function of temperature for films including pectin according to the present invention.
Figure 7B:
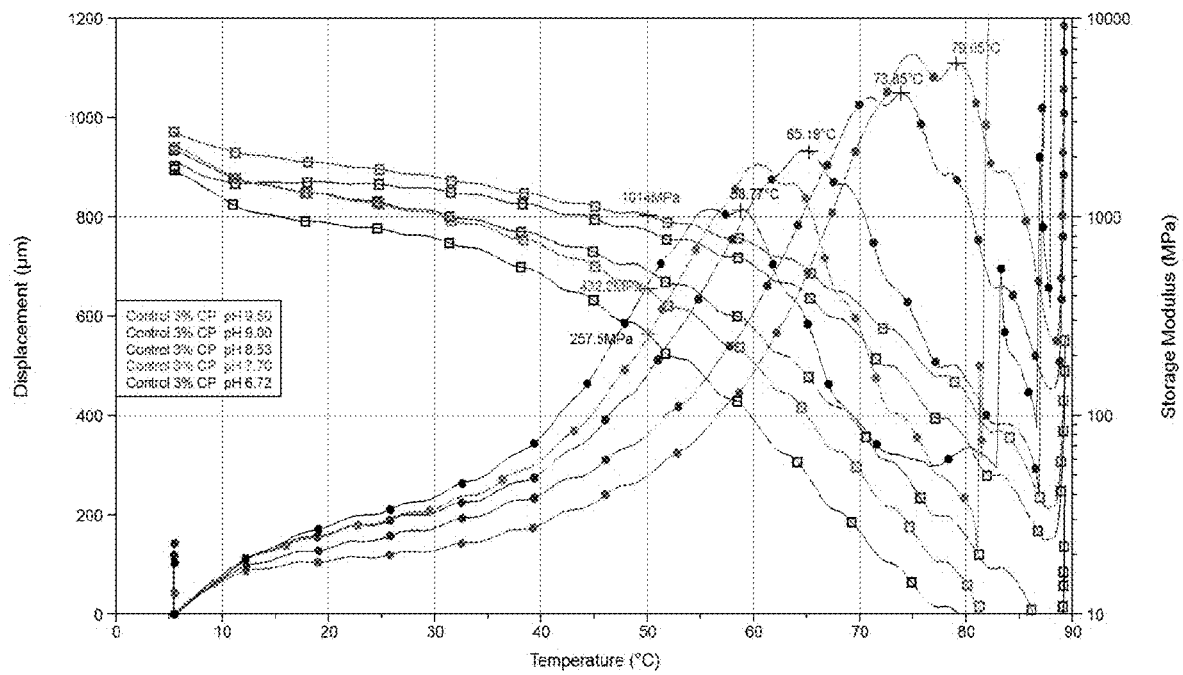
FIG. 7B shows measurements of storage modulus (E', MPa) and displacement as a function of temperature for films including pectin according to the present invention.
Figure 8:
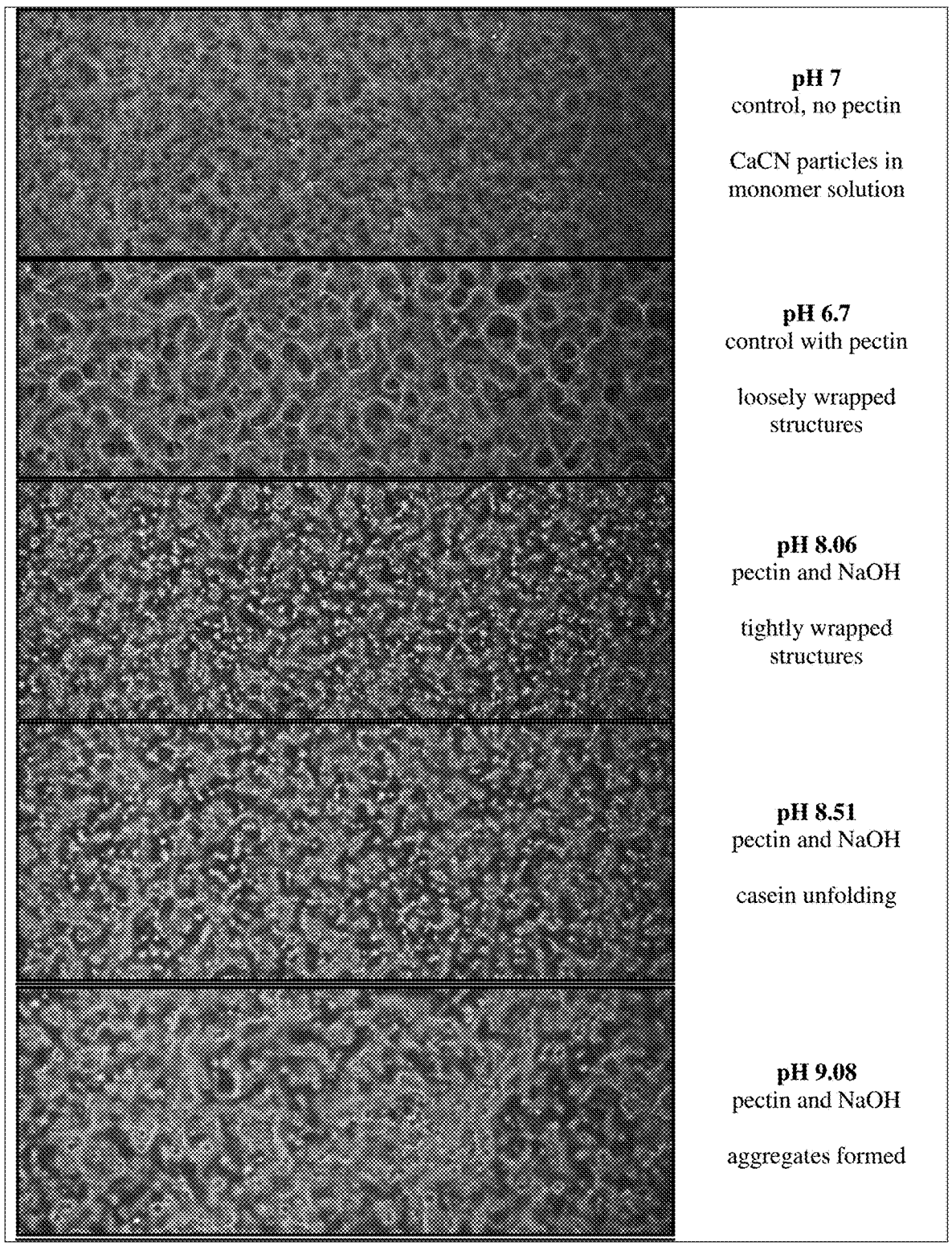
FIG. 8 shows micrographs at 20× magnification of films including pectin according to the present invention.

Films made using a strengthening additive. Exemplary films were cast and characterized using the above method and formulation (C). The pH of the suspensions was varied from 6.74 (unmodified control) to 9.54 using NaOH, and the amount of pectin in the suspension was adjusted by adding pectin, for example in the form of a concentrated solution of CP, to the suspension to achieve a desired final concentration, such as approximately 3% (w/w) final concentration. Results of mechanical testing are shown in FIG. 7A and FIG. 7B. As can be seen, the best performing pH values tested were at 8.53 and 9.50, with a localized minimum at 9.00. Microscopy images of replicates of these films are shown in FIG. 8. In particular, the unfolding and spreading of casein can be seen in the pH 8.51 image, but at a pH of 9.08, some aggregates have formed, which may explain the localized minimum of physical properties seen in the mechanical testing. Dry films produced using formulation (C) and substituting Ca(OH)$_2$ for NaOH as the alkaline additive were also produced as displayed similar structure up through a pH of 9.0. At a pH of 9.5 however, large caseinate/pectin aggregates formed (data not shown).

Figure 9A:
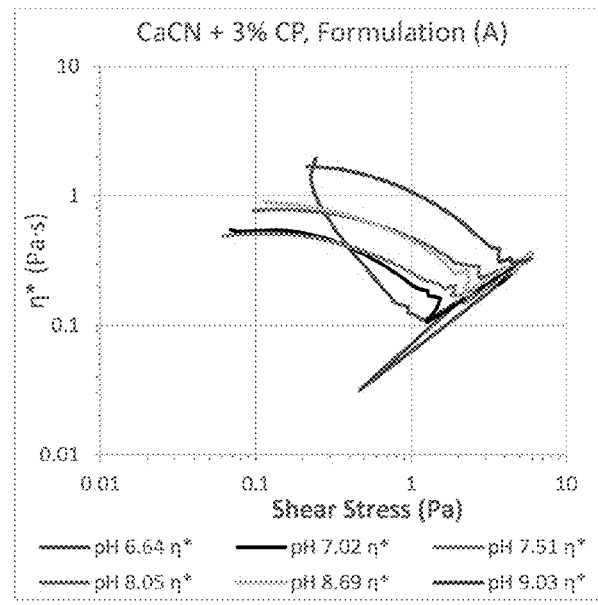
FIG. 9A shows rheology studies of suspensions according to formulation (A), described herein.
Figure 9B:
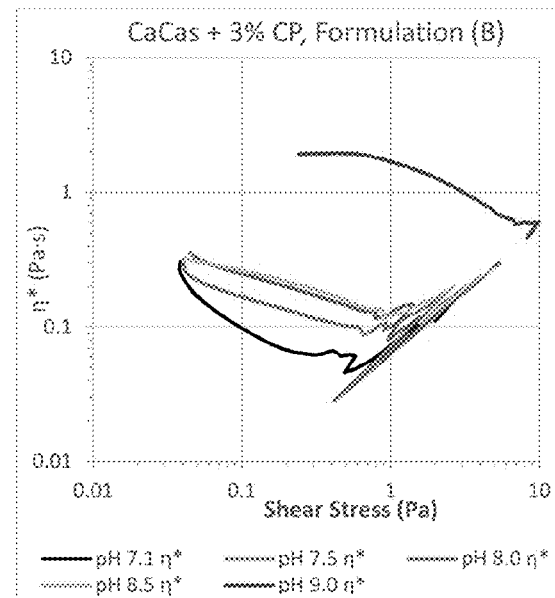
FIG. 9B shows rheology studies of suspensions according to formulation (B), described herein.
Figure 9C:
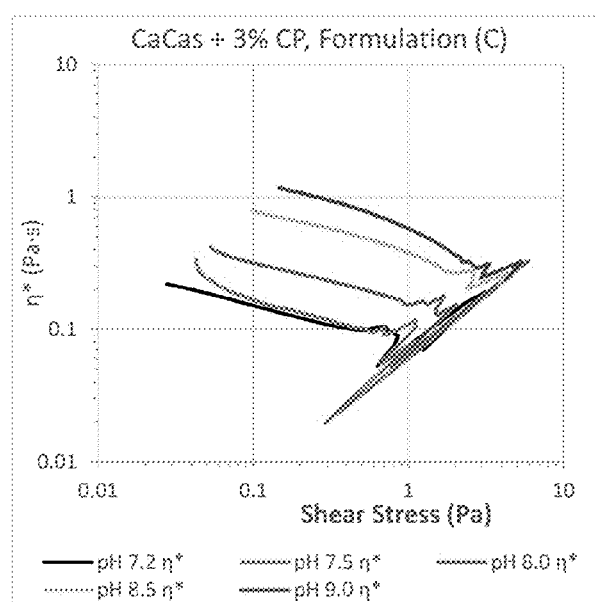
FIG. 9C shows rheology studies of suspensions according to formulation (C), described herein.

Rheology of suspensions containing a strengthening additive. Suspensions of all three of the above formulations (A), (B), and (C) were tested at varying pHs to determine if the order of addition would change how the suspension would react to increasing alkalinity. The results of these tests, using NaOH to increase alkalinity, are shown in FIGS. 9A, 9B, and 9C (corresponding to formulations (A), (B), and (C), respectively). As can be seen, the order of addition certainly makes a difference. In particular, though increased alkalinity increases the viscosity and strength of the gel at least through a pH of 8.0, above 8.0 the behavior of the suspension changes. For formulation (C), the change continues progressively through a pH of 9, whereas in formulation (B), there is little change to a pH of 8.5, but then a jump at a pH of 9. Furthermore, formulation (A) appears to show a local minimum at a pH of about 8.7 before the strength increases more at a pH of 9.

Example 4: Films From Dry Milk

As an alternative casein source, nonfat dry milk powder (NFDM) was used to create films, both as the sole casein and also as a source mixed together with CaCN. Suspensions were prepared with either 3:1 NFDM/Gly or 1.5:1.5:1 NFDM/CaCN/Gly, and then either non-adjusted (control), or pH adjusted using Ca(OH)$_2$ to a pH of 8, 9, 10, 11, or 12. NFDM, which contains micellar casein, was not expected to behave in the same fashion as a caseinate, in that the preferred pH value and/or the preferred composition may be different from those found in the above experiments. However, using the same methods and testing described above, the inventors were able to elucidate which of the tested films would be preferably in at least some embodiments of the invention.

In all cases, the adjusted films possessed better mechanical properties than the controls (no pH adjustment), with less or no visible lactose crystallization, and sharp structural changes as evidenced by the drastic changes in foaming behaviors between pH 7 and 8, and then between pH 10 and 11. The clearest and strongest films for both formulations were produced at pH values of 11 and 12. A summary of the films produced is given in Table 3 below:

TABLE 3

Summary of NFDM films

| pH | NFDM/Gly | NFDM/CaCas/Gly |
|---|---|---|
| Control (pH 6.4-6.6) | White<br>No bubbles<br>Brittle and weak | Clear<br>Hazy, no bubbles<br>Strong and stiff |
| 8.0 | Less white<br>Few bubbles<br>Pliable but weak | Clear<br>Lots of bubbles<br>Strong and flexible |
| 9.0 | Less white<br>Some bubbles<br>Pliable but weak | Clear<br>Lots of bubbles<br>Strong and flexible |
| 10.0 | Less white<br>Most bubbles<br>Pliable but weak | Clear<br>Lots of bubbles<br>Strong and flexible |
| 11.0 | CLEAR<br>No bubbles<br>Pliable, stretchy and strong | CLEAR<br>No bubbles<br>Stronger, more flexible |
| 12.0 | CLEAR<br>No bubbles<br>flexible, stretchy and strong | CLEAR<br>No bubbles<br>Strongest, most flexible |

Figure 10:
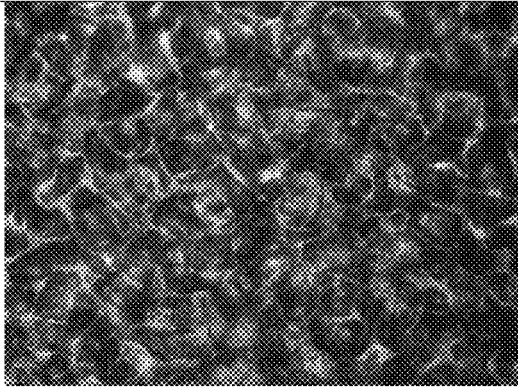
FIG. 10 shows micrographs at 20× magnification of films including nonfat dry milk (NFDM) according to the present invention.
Figure 10:
Figure 10:
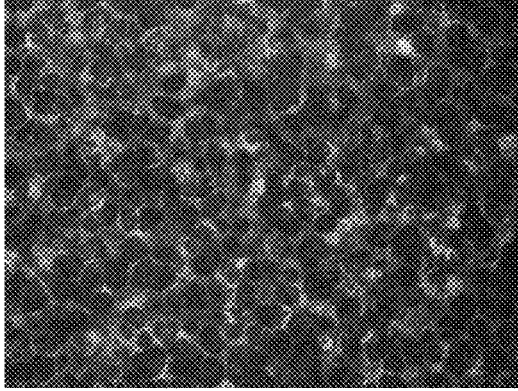
Figure 10:
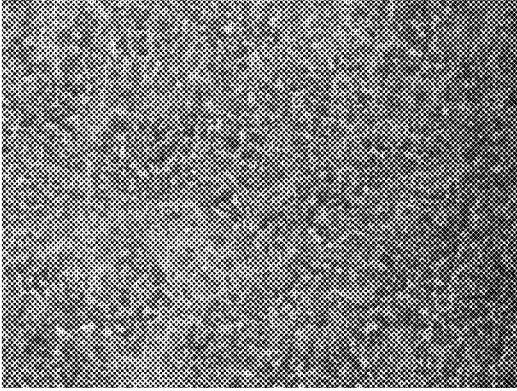
Figure 10:
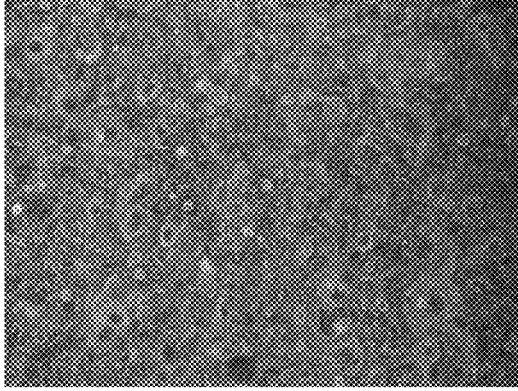
Figure 10:
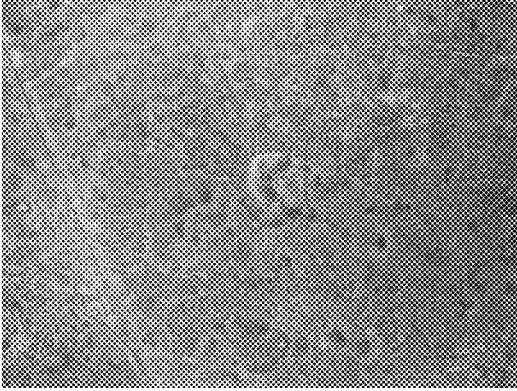
Figure 11:
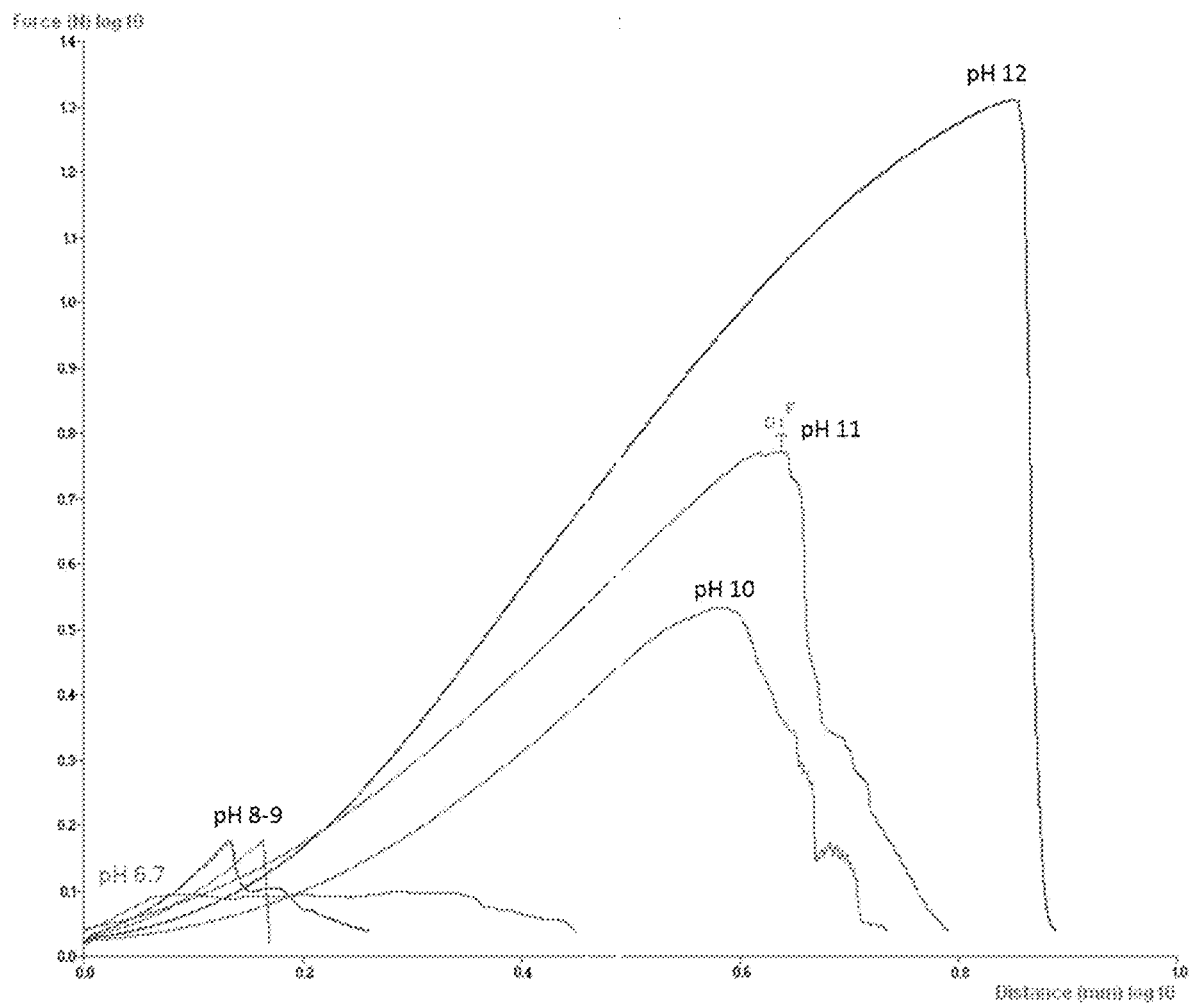
FIG. 11 shows tensile properties of films containing NFDM as measured with a burst test.
Figure 12A:
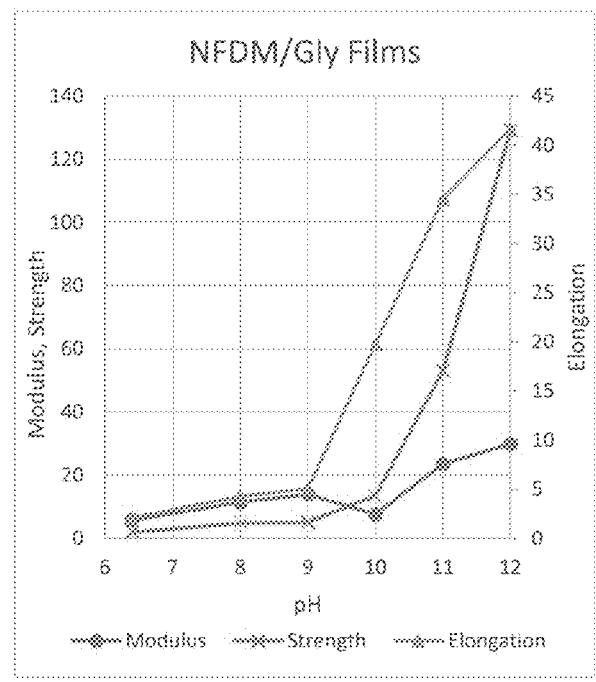
FIG. 12A shows measurements of storage modulus and elongation (displacement) as a function of pH for films made with NFDM as the sole casein source according to the present invention.
Figure 12B:
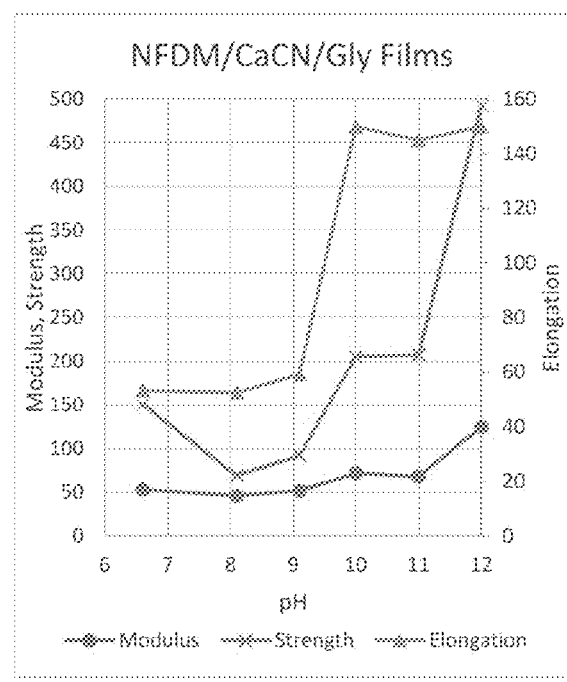
FIG. 12B shows measurements of storage modulus and elongation (displacement) as a function of pH for films made with NFDM and calcium caseinate as the casein source according to the present invention.
Figure 12C:
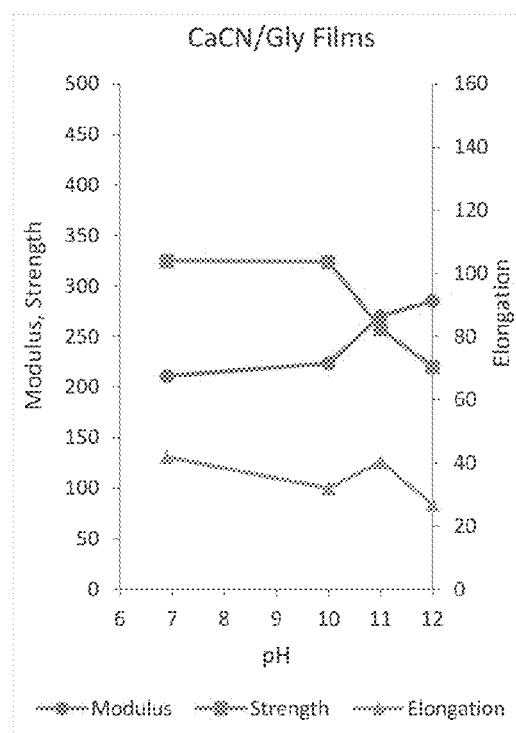
FIG. 12C shows measurements of storage modulus and elongation (displacement) as a function of pH for films made with calcium caseinate as the sole casein source according to the present invention.

Shown in FIG. 10 are micrographs at 20× magnification of selected films. The images show a progression from little or no addition of Ca(OH)$_2$ to sufficient to reach a pH of 11 causing a physical change in the films from a brittle structure with large crystalline deposits to a smooth, more uniform film. Further, mechanical testing was done on the films. FIG. 11 shows the results of tensile testing (burst-test) on films made from 3:1 NFDM/Gly. Comparative results of mechanical testing with films made from NFDM, NFDM/CaCN, and CaCN are shown in FIGS. 12A, 12B, and 12C with some of the results summarized in Table 4 below:

TABLE 4

Results of mechanical testing on NFDM films (normalized over thickness)

| pH | Film type | Modulus N/mm$^2$ | Strength N/mm | Elongation mm/mm |
|---|---|---|---|---|
| 6.4 | NFDM | 5.7 | 1.9 | 2.1 |
| 8 | NFDM | 11.4 | 4.7 | 4.3 |
| 9 | NFDM | 13.9 | 5.0 | 5.0 |
| 10 | NFDM | 7.6 | 13.5 | 19.8 |
| 11 | NFDM | 23.5 | 52.9 | 34.5 |
| 12 | NFDM | 29.8 | 129.2 | 41.6 |
| 6.6 | NFDM/CaCN | 53 | 151 | 53 |
| 8.1 | NFDM/CaCN | 46 | 69 | 52 |

TABLE 4-continued

Results of mechanical testing on NFDM films (normalized over thickness)

| pH | Film type | Modulus N/mm$^2$ | Strength N/mm | Elongation mm/mm |
|---|---|---|---|---|
| 9.1 | NFDM/CaCN | 51 | 92 | 59 |
| 10 | NFDM/CaCN | 72 | 205 | 150 |
| 11 | NFDM/CaCN | 68 | 207 | 145 |
| 12 | NFDM/CaCN | 125 | 492 | 150 |
| 6.9 | CaCN | 211 | 325 | 42 |
| 10 | CaCN | 224 | 324 | 32 |
| 11 | CaCN | 270 | 257 | 40 |
| 12 | CaCN | 285 | 220 | 27 |

As can be seen in the figures and the table above, the control films were stiff and brittle, showing little strength. NFDM films at about pH of 8 and 9 were improved compared to the control, although those made from NFDM/CaCN either did not improve, or even showed some decrease in strength through a pH of about 9. Above a pH of 9 however, both of the NFDM-containing films performed demonstrably and significantly better than films created at lower pH values. This sharp change between a pH of 9 and a pH of 10 indicates a structural change in the film structure, which agrees with the micrographs shown in FIG. 10, as discussed above. However, in the same high pH range of 11-12, the CaCN (no NFDM) films became stiff and slightly brittle. The data suggest that the NFDM/CaCN ratio could be varied within a wide range to achieve desired mechanical properties for a particular application.

Example 5: Water Resistance

Different variations of the above-described films were tested with regard to water resistance by placing squares of film in water and visually determining how long until the films lose integrity and/or dissolve. The results of these tests are summarized in Tables 5.1-5.3 below. The tables are split into series based upon the age of the films, such that results can be consistently compared within a series.

TABLE 5.1

Water solubility test results, Series 1 (films of a few months old)

| Casein source | Ratio of casein source:glycerol | % Pectin | Formulation (A), (B), or (C) | Alkaline additive | pH | Length of min until dissolution |
|---|---|---|---|---|---|---|
| CaCN | 3:1 | 1 | (B) | none | 6.7 | 8 |
| CaCN | 3:1 | 3 | (B) | NaOH | 8.07 | 20 |
| CaCN | 3:1 | 3 | (B) | NaOH | 8.54 | 13 |
| CaCN | 3:1 | 3 | (B) | NaOH | 9.02 | 35 |
| NaCN | 3:1 | 3 | (C) | none | 6.6 | <1 |
| NaCN | 3:1 | 3 | (C) | NaOH | 8.01 | 11 |
| NaCN | 3:1 | 3 | (C) | NaOH | 8.55 | 30 |
| NaCN | 3:1 | 3 | (C) | NaOH | 9.02 | >37 |

TABLE 5.2

Water solubility test results, Series 2 (films of about a year old)

| Casein source | Ratio of casein source:glycerol | % Pectin | Formulation (A), (B), or (C) | Alkaline additive | pH | Length of min until dissolution |
|---|---|---|---|---|---|---|
| CaCN | 3:1 | 0 | N/A | none | 7.1 | 25 |
| CaCN | 3:1 | 0 | N/A | Ca(OH)$_2$ | 7.6 | 65 |
| CaCN | 3:1 | 0 | N/A | Ca(OH)$_2$ | 8.0 | 35 |
| CaCN | 3:1 | 0 | N/A | Ca(OH)$_2$ | 8.5 | 75 |
| CaCN | 3:1 | 0 | N/A | Ca(OH)$_2$ | 9.1 | 104 |
| CaCN | 3:1 | 0 | N/A | Ca(OH)$_2$ | 9.6 | 120 |

TABLE 5.3

Water solubility test results, Series 3 (fresh films, less than a day old)

| Casein source | Ratio of casein source:glycerol | % Pectin | Formulation (A), (B), or (C) | Alkaline additive | pH | Length of min until dissolution |
|---|---|---|---|---|---|---|
| CaCN | 3:1 | 0 | N/A | none | 6.99 | 3 |
| CaCN | 3:1 | 3 | (C) | none | 6.66 | 3 |
| CaCN | 3:1 | 3 | (C) | Ca(OH)$_2$ | 7.52 | 3 |
| CaCN | 3:1 | 3 | (C) | Ca(OH)$_2$ | 8.03 | 6 |
| CaCN | 3:1 | 3 | (C) | Ca(OH)$_2$ | 8.53 | 3 |
| CaCN | 3:1 | 3 | (C) | Ca(OH)$_2$ | 9.04 | 7 |
| CaCN | 3:1 | 3 | (C) | Ca(OH)$_2$ | 9.53 | >10 |

As can be seen in tables, resistance to water generally tracks along the other physical properties tested and disclosed herein. Specifically, the control films all dissolved much quicker than the pH-adjusted films, and both films with and without pectin displayed a "local minimum" effect, as seen in the third row of Table 5.1 and the third row of Table 5.2, further underlining the complex and unexpected physical changes effected by the addition of an alkaline additive.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A casein-based film, comprising:
   a casein source;
   a plasticizer; and
   an alkaline additive,
   wherein the film has a melting point temperature at 50% relative humidity of at least 60° C., and
   wherein the alkaline additive is in an amount in excess of an amount necessary to convert all casein in the mixture to caseinate.

2. The casein-based film of claim 1, wherein the film has a storage modulus, G', at 50% relative humidity and 60° C., of at least 150 MPa.

3. The casein-based film of claim 1, wherein the casein source is one of a caseinate, a fluid or dried milk product, milk protein concentrate, micellar casein concentrate, and a mixture thereof.

4. The casein-based film of claim 1, wherein the plasticizer is one of glycerol, sorbitol, propylene glycol, polypropylene glycol, sucrose, and a mixture thereof.

5. The casein-based film of claim 1, wherein the amounts of the casein source and the plasticizer are present in a ratio of casein source:plasticizer being 99:1 to 1:1.

6. The casein-based film of claim 1, further comprising a strengthening additive.

7. The casein-based film of claim 6, wherein the strengthening additive is one of a pectin, a polysaccharide, a pullulan-microbial polysaccharide, a dextrin, an oligosaccharides, a monosaccharide, a disaccharide, high fructose corn syrup, cellulose, hemi-cellulose, a gum or the constitutive sugar thereof, methylcarboxycellulose, gelatin, carrageenan, agar, an alginates, egg albumen, transglutaminase, tyrosinase, an aglycone, a glycoside, a chloride salt, a bicarbonates, a phosphate, one of vitamins A-K, milk fat, a polyunsaturated fat, a monosaturated fat, an omega-3 fatty acid, a conjugated linolenic acid, alpha linolenic acid, a phospholipid from milkfat, a lecithin, a sterol, soluble or insoluble plant fiber, a fiber gum, psyllium, flax seed, quince seed, an antioxidant, a carotenoid, and a mixture thereof.

8. The casein-based film of claim 6, wherein the strengthening additive is present in an amount of 0.05% to 5% (w/w).

9. A method of producing a casein-based film, comprising:
   producing a film-production suspension, the film-production suspension comprising a solvent, a casein source, and a plasticizer;
   adjusting the pH of the film-production solution to at least ≥8.0;
   creating a film from the pH-adjusted film-production suspension by drying; and
   thereby obtaining a casein-based film.

10. The method of claim 9, wherein the solvent is water.

11. The method of claim 9, wherein the casein source is one of a caseinate, a fluid or dried milk product, a milk protein concentrate, a micellar casein concentrate, and a mixture thereof.

12. The method of claim 9, wherein the plasticizer is one of glycerol, sorbitol, propylene glycol, polypropylene glycol, sucrose, and a mixture thereof.

13. The method of claim 9, wherein the amounts of the casein source and the plasticizer are present in the film-production suspension in a ratio of casein source:plasticizer being 99:1 to 1:1.

14. The method of claim 9, wherein the film-production suspension further comprises a strengthening additive.

15. The method of claim 14, wherein the producing of the film-production suspension is performed by either:
   (i) adding the plasticizer to the solvent to create a solvent-plasticizer suspension, then adding the casein source to the plasticizer-solvent suspension to create a solvent-plasticizer-casein suspension, then adding the strengthening additive to create the film-production suspension;
   (ii) adding the plasticizer to the solvent to create a solvent-plasticizer suspension, then adding the strengthening additive to create a solvent-plasticizer-strengthening additive suspension, then adding the casein source to the solvent-plasticizer-strengthening additive suspension to create the film-production suspension; or
   (iii) adding the strengthening additive to the solvent to create a solvent-strengthening additive suspension, then adding the casein source to the solvent-strengthening additive suspension to create a solvent-strengthening additive-casein suspension, then adding the plasticizer to the solvent-strengthening additive-casein suspension to create the film-production suspension.

16. The method of claim 14, wherein the strengthening additive is one of pectin, a polysaccharide, a pullulan-microbial polysaccharide, a dextrin, an oligosaccharides, a monosaccharide, a disaccharide, high fructose corn syrup, cellulose, hemi-cellulose, a gum or the constitutive sugar thereof, methylcarboxycellulose, gelatin, carrageenan, agar, an alginates, egg albumen, transglutaminase, tyrosinase, an aglycone, a glycoside, a chloride salt, a bicarbonates, a phosphate, one of vitamins A-K, milk fat, a polyunsaturated fat, a monosaturated fat, an omega-3 fatty acid, a conjugated linolenic acid, alpha linolenic acid, a phospholipid from milkfat, a lecithin, a sterol, soluble or insoluble plant fiber, a fiber gum, psyllium, flax seed, quince seed, an antioxidant, a carotenoid, and a mixture thereof.

17. The method of claim 9, wherein the adjusting the pH of the film-production suspension comprises adding an alkaline additive to the film-production suspension.

18. The method of claim 17, wherein the alkaline additive is one of a monovalent hydroxide, a divalent hydroxide, and ammonium.

19. The method of claim 9, wherein the adjusting the pH of the film-production suspension comprises adjusting the pH to at least ≥8.5.

20. The method of claim 19, wherein the adjusting the pH of the film-production suspension comprises adjusting the pH to at least ≥9.0.

21. The method of claim 19, wherein the adjusting the pH of the film-production suspension comprises adjusting the pH to at least ≥9.4.

22. The method of claim 9, wherein the adjusting the pH of the film-production suspension comprises adjusting the pH to a value of about 8.5 to about 12.0.

23. The method of claim 9, wherein the creating of the film from the pH-adjusted film-production suspension by drying comprises one of casting a film in mold, spraying, and dipping.

24. The casein-based film produced by the method of claim 9.

* * * * *